(12) United States Patent
Chen et al.

(10) Patent No.: US 11,006,670 B2
(45) Date of Patent: May 18, 2021

(54) ATOMIZER FOR ELECTRONIC CIGARETTE

(71) Applicant: Shenzhen First Union Technology Co., Ltd., Shenzhen (CN)

(72) Inventors: Zhiquan Chen, Shenzhen (CN); Yonghai Li, Shenzhen (CN); Zhongli Xu, Shenzhen (CN); Xiaoqiang Zhao, Shenzhen (CN)

(73) Assignee: Shenzhen First Union Technology Co., Ltd., Guangdong (CN)

( * ) Notice: Subject to any disclaimer, the term of this patent is extended or adjusted under 35 U.S.C. 154(b) by 407 days.

(21) Appl. No.: 15/871,776

(22) Filed: Jan. 15, 2018

(65) Prior Publication Data

US 2018/0199631 A1    Jul. 19, 2018

(30) Foreign Application Priority Data

Jan. 16, 2017   (CN) .......................... 201710029115.7
Jan. 16, 2017   (CN) .......................... 201720047525.X

(51) Int. Cl.
| | |
|---|---|
| *A24F 47/00* | (2020.01) |
| *A24F 40/50* | (2020.01) |
| *A24F 40/485* | (2020.01) |
| *A61M 11/04* | (2006.01) |
| *A61M 15/06* | (2006.01) |

(52) U.S. Cl.
CPC .......... *A24F 47/008* (2013.01); *A24F 40/485* (2020.01); *A24F 40/50* (2020.01); *A61M 11/042* (2014.02); *A61M 15/06* (2013.01); *A61M 2205/121* (2013.01); *A61M 2205/128* (2013.01)

(58) Field of Classification Search
CPC ...... A24F 47/008; A24F 40/485; A24F 40/50; A61M 11/042; A61M 15/06; A61M 2205/12; A61M 2205/121

USPC ......................................................... 392/406
See application file for complete search history.

(56) References Cited

FOREIGN PATENT DOCUMENTS

| | | |
|---|---|---|
| CN | 105 212 278 A | 1/2016 |
| CN | 205 456 070 U | 8/2016 |
| CN | 105 962 420 A | 9/2016 |
| WO | 2017/166263 A1 | 10/2017 |

OTHER PUBLICATIONS

Chinese to English machine translation of CN 105962420, Published in 2016.*

* cited by examiner

*Primary Examiner* — Erin E McGrath
(74) *Attorney, Agent, or Firm* — Proi Intellectual Property US; Klaus Michael Schmid

(57) ABSTRACT

An atomizer for an electronic cigarette is disclosed, including: a housing unit defining therein a tobacco liquid chamber configured for storing a tobacco liquid; a first casing body defining thereon a first liquid guide hole configured for allowing the tobacco liquid to pass through; an atomization device; a control valve configured for closing or opening the first liquid guide hole to control the tobacco liquid to enter the atomization device; and a base assembly detachably connected to the housing unit and supporting the atomization device and configured to be in linkage with the control valve. The base assembly can drive the control valve to close the first liquid guide hole while the base assembly is detached from the housing unit. The base assembly can drive the control valve to open the first liquid guide hole while the base assembly is assembled on the housing unit.

16 Claims, 9 Drawing Sheets

ATOMIZER FOR ELECTRONIC CIGARETTE

CROSS REFERENCE TO RELATED APPLICATIONS

The present application claims priority to Chinese patent application CN 201710029115.7 filed on Jan. 16, 2017 and to Chinese utility model CN 201720047525.X filed on Jan. 16, 2017.

TECHNICAL FIELD

The present disclosure relates to the field of smoking sets, and particularly, to an atomizer for an electronic cigarette.

BACKGROUND

In the prior art, typical electronic cigarette atomizers all include a separate detachable atomization device. As a core assembly in the atomizer to generate an aerosol, the atomization device can be replaced conveniently at any time. Electronic cigarette atomizers available on the current market mostly adopt a manner of replacing the atomization device directly from the top part or bottom part. The atomization device is in communication with a tobacco liquid chamber in the atomizer. When the tobacco liquid chamber is not closed in time, if the tobacco liquid chamber has remaining tobacco liquid when the atomization device is replaced, the tobacco liquid is easy to leak, thereby impacting user experience. In addition, the above electronic cigarette atomizers mostly have a liquid refill function. Since a channel between the tobacco liquid chamber and the atomization device is not closed when tobacco liquid is refilled, after the tobacco liquid is refilled, the internal-external air pressure difference of the tobacco liquid chamber is easy to cause the insufficient liquid blocking force to lead to leakage of tobacco liquid and thus to impact user experience.

SUMMARY

The technical problem to be solved by the present disclosure is to remedy the drawbacks in the prior art by providing an atomizer for an electronic cigarette capable of closing a tobacco liquid chamber. The electronic cigarette atomizer avoids leakage of tobacco liquid when replacing an atomization device.

In order to solve the above technical problem, the present disclosure provides an atomizer for an electronic cigarette. The atomizer includes: a housing unit, the housing unit defining therein a tobacco liquid chamber configured for storing a tobacco liquid; a first casing body located in the tobacco liquid chamber, the first casing body defining thereon a first liquid guide hole configured for allowing the tobacco liquid to pass through; an atomization device located inside the first casing body, the atomization device being configured for aerosolizing the tobacco liquid to generate an aerosol for a user to inhale; a control valve, the control valve being configured for closing or opening the first liquid guide hole to control the tobacco liquid to enter the atomization device; and a base assembly detachably connected to the housing unit and supporting the atomization device, the base assembly being configured to be in linkage with the control valve, the base assembly being capable of driving the control valve to close the first liquid guide hole while the base assembly is detached from the housing unit, and the base assembly being capable of driving the control valve to open the first liquid guide hole while the base assembly is assembled on the housing unit.

As an embodiment of the present disclosure, the control valve includes a second casing body located between the first casing body and the atomization device, the second casing body defines thereon a second liquid guide hole configured for allowing the tobacco liquid to pass through, and the base assembly is capable of driving the second casing body to rotate so that the second liquid guide hole and the first liquid guide hole are staggered or overlapped.

Further, the second casing body is configured to be in threaded connection with the base assembly, and the second casing body has a threaded portion disposed at the lower end thereof.

Further, the tobacco liquid chamber has a fixing sleeve disposed at the bottom thereof, the fixing sleeve being configured for fixing the first casing body and the second casing body, and the second casing body is capable of rotating relative to the fixing sleeve.

Further, the second casing body has a flange disposed on a side wall thereof, the flange has a rotation angle limit groove concaved inwards, and the fixing sleeve has a stop block disposed on an inner side thereof, the stop block being matched with the rotation angle limit groove.

Preferably, the rotation angle limit groove has a corresponding arc angle of 45 degrees.

Further, the second casing body defines a notch in a lower end thereof, the atomization device has a projecting portion disposed on an outer side thereof, and, when the atomization device is inserted in to the second casing body, the projecting portion enters the notch so as to prevent rotation occurring between the atomization device and the second casing body.

Further, the base assembly includes an outer threaded sleeve configured to be in threaded connection with the second casing body, and an electrode column located at the center of the outer threaded sleeve and insulated from the outer threaded sleeve.

Further, the atomization device includes an outer electrode portion configured to be abutted against the outer threaded sleeve and an inner electrode portion configured to be abutted against the electrode column.

Further, the atomization device includes an outer sleeve, a heating element located in the outer sleeve, and a liquid storage layer surrounding the periphery of the heating element.

Specifically, the outer sleeve defines a liquid inlet hole in a side wall thereof, the liquid inlet hole being capable of communicating with the first liquid guide hole and the second liquid guide hole.

Further, in order to realize liquid refill function, the atomizer further includes a cover body assembly detachably connected to an upper end of the housing unit, the tobacco liquid chamber defines a liquid refill port configured for refilling tobacco liquid in an upper part thereof, and the covey body assembly is configured for sealing the liquid refill port.

Further, the cover body assembly is configured to be in linkage with the first casing body; while the cover body assembly is detached from the housing unit, the cover body assembly is capable of driving the first casing body to rotate and allowing the first liquid guide hole to be closed, thereby preventing the tobacco liquid flowing into the atomization device; and, while the cover body assembly is assembled on the housing unit, the cover body assembly is capable of driving the first casing body to rotate and allowing the first liquid guide hole to be opened.

Further, the cover body assembly includes a cover body, an outer tube connected to the cover body, and an inner tube located in the outer tube, the outer tube being configured to be in threaded connection with the first casing body.

Further, the first casing body has a plurality of screw threads disposed on an inner wall at the upper end thereof and defines an arc groove on a lower edge thereof, the arc groove being configured for limiting the range of rotation angle of the first casing body.

Preferably, the arc groove has an angle of 45 degrees.

Further, the inner tube extends into the first casing body and is aligned to the atomization device, the cover body has an air inlet disposed thereon, an annular space is defined between the inner tube, the outer tube and the first casing body, the annular space forms an air inlet passage, the air inlet passage is configured to be in communication with the air inlet, and the inner tube defines an air outlet passage therein.

In addition, the tobacco liquid chamber also can be closed when tobacco liquid is refilled. The present disclosure further provides an atomizer. The atomizer includes: a housing unit, the housing unit defining therein a tobacco liquid chamber configured for storing a tobacco liquid, and the tobacco liquid chamber having a liquid refill port; a first casing body located in the tobacco liquid chamber, the first casing body defining thereon a first liquid guide hole configured for allowing the tobacco liquid to pass through; an atomization device located inside the first casing body, the atomization device being configured for aerosolizing the tobacco liquid to generate an aerosol for a user to inhale; and a cover body assembly detachably connected to the housing unit and sealing the liquid refill port, the cover body assembly being configured to be in linkage with the first casing body; while the cover body assembly is detached from the housing unit, the cover body assembly being capable of driving the first casing body to rotate and allowing the first liquid guide hole to be closed, thereby preventing the tobacco liquid flowing into the atomization device; and, while the cover body assembly is assembled on the housing unit, the cover body assembly being capable of driving the first casing body to rotate and allowing the first liquid guide hole to be opened.

The beneficial effects of the present disclosure are as follows. The control valve and the base assembly are configured to be in linkage in the present disclosure. When the atomization device is to be replaced, the base assembly can be detached to drive the control valve to close the first liquid guide hole on the first casing body. Since the first liquid guide hole is closed, the remaining tobacco liquid in the tobacco liquid chamber will not flow out; thus, user experience is improved. After the atomization device is replaced, the base assembly can be assembled to drive the control valve to open the first liquid guide hole again. In this condition, the tobacco liquid can flow into the atomization device successfully. In addition, after the base assembly and the atomization device are removed, the atomizer in the present disclosure can still refill tobacco liquid into the tobacco liquid chamber without leakage of tobacco liquid. The use convenience of the product is improved.

DETAILED DESCRIPTION

The structure and operating principle of the electronic cigarette atomizer capable of closing a tobacco liquid chamber provided by the present disclosure are illustrated below in further detail through exemplary embodiments.

Figure 1:
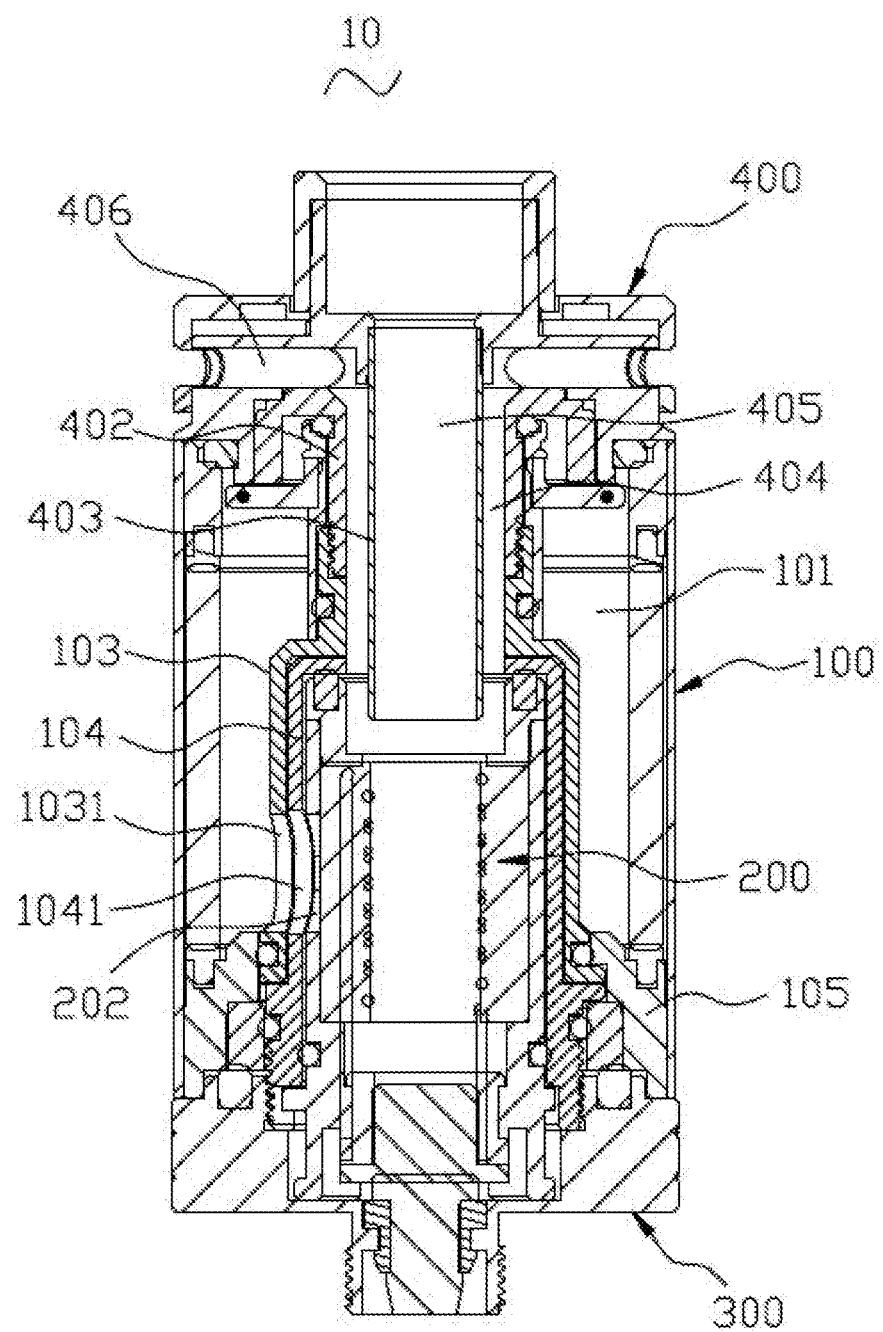
FIG. 1 is a diagram illustrating a state in which a base assembly and an atomization device are assembled on a housing unit in an atomizer for an electronic cigarette provided by an embodiment.

Referring to FIG. 1, the present embodiment provides an atomizer 10 for an electronic. The atomizer 10 includes a housing unit 100, an atomization device 200 located in the housing unit 100, a base assembly 300 detachably connected to the housing unit 100, and a cover body assembly 400 detachably connected to the housing unit 100. The housing unit 100 defines therein a tobacco liquid chamber 101 configured for storing a tobacco liquid. The tobacco liquid chamber 101 has a first casing body 103 disposed therein. The first casing body 103 defines thereon a first liquid guide hole 1031 configured for allowing the tobacco liquid to pass through. The atomization device 200 is located inside the first casing body 103 and is configured for aerosolizing the tobacco liquid to generate an aerosol for a user to inhale. The first casing body 103 is in tubular shape and covers the atomization device 200. The atomization device 200 and the tobacco liquid chamber 101 are isolated from each other, but are capable of communicating with each other through the first liquid guide hole 1031.

In order to close the tobacco liquid chamber 101, the atomizer 10 in the present embodiment further includes a control valve. The control valve is mounted between the first casing body 103 and the atomization device 200 and is configured for closing or opening the first liquid guide hole 1031 to control the tobacco liquid to enter the atomization device 200. Specifically, the base assembly 300 is detachably connected to the housing unit 100 and supports the atomization device 200. The atomization device 200 is located inside the first casing body 103, that is to say, a user can take the atomization device 200 out to replace by detaching the base assembly 300. The base assembly 300 is configured to be in linkage with the control valve. When the atomizer 10 works normally, the control valve does not block the first liquid guide hole 1031, and the tobacco liquid in the tobacco liquid chamber 101 can flow to the atomization device 200 successfully through the first liquid guide hole 1031. While the base assembly 300 is detached from the housing unit 100, the base assembly 300 is capable of driving the control valve to close the first liquid guide hole 1031. Therefore, the user can replace the atomization device 200 without worrying the leakage of tobacco liquid, and use experience is improved. While the base assembly 300 is assembled on the housing unit 100, the base assembly 300 is capable of driving the control valve to open the first liquid guide hole 1031 again.

In the present embodiment, the control valve can be in tubular shape, circular ring shape, or arc sheet shape. The control valve fits the interior of the first casing body 103 in a sealed manner and is capable of rotating relative to the first casing body 103. The control valve may have various movement modes. For example, the control valve is in horizontal linkage with the base assembly 300, the base assembly 300 is capable of driving the control valve to rotate while the base assembly 300 is rotating, and the control valve closes the first liquid guide hole 1031 or opens the first liquid guide hole 1031 during the rotating process. In another example, the control valve is in axial linkage with the base assembly 300, the base assembly 300 is capable of driving the control valve to move upwards and downwards along the axial direction, so as to expose the first liquid guide hole 1031 or block the first liquid guide hole 1031.

Figure 3:
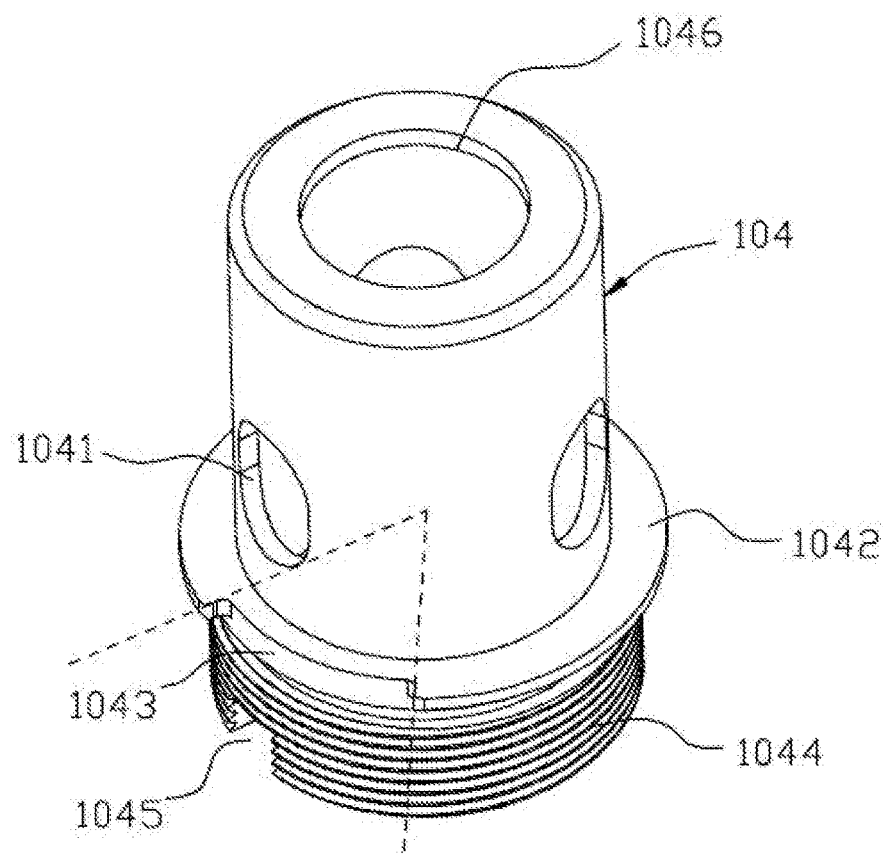
FIG. 3 is a structure diagram of a second casing body according to an embodiment.

Referring to FIG. 3 and FIG. 1, as a preferred embodiment of the present disclosure, the control valve includes a second casing body 104 located between the first casing body 103 and the atomization device 200. The second casing body 104 defines thereon a second liquid guide hole 1041 configured for allowing the tobacco liquid to pass through, and the base assembly 300 is capable of driving the second casing body 104 to rotate so that the second liquid guide hole 1041 and the first liquid guide hole 1031 are staggered or overlapped (i.e., misaligned or aligned). The operating principle of the control valve is described below by taking the second casing body 104 for example.

The second casing body 104 is in tubular shape. The second liquid guide hole 1041 is provided as multiple ones, which are evenly distributed on a side wall of the second casing body 104 at intervals. The second liquid guide hole 1041 and the first liquid guide hole 1031 are at the same horizontal position. The second casing body 104 further defines an airflow opening 1046 at the top end thereof. In the present embodiment, the second casing body 104 is preferably in threaded connection with the base assembly 300, and the second casing body 104 has a threaded portion 1044 disposed at the lower end thereof. While a user screws the base assembly 300, the base assembly 300 first can drive the second casing body 104 to rotate due to the friction force between the base assembly 300 and the second casing body 104. When the second casing body 104 rotates to the final position, the base assembly 300 can continue rotating to be screwed to the second casing body 104 or screwed off the second casing body 104.

It should be noted that in the present embodiment the base assembly 300 is connected to a lower end of the housing unit 100 and a user can detach the base assembly 300 from the lower end to replace the atomization device 200. Depending on different preferences of users, the base assembly 300 in the present disclosure can also be designed to be connected to an upper end of the housing unit 100, so that the user can detach the base assembly 300 from the upper end to replace the atomization device 200. Therefore, the threaded portion 1044 on the second casing body 104 can also be disposed on the upper end of the second casing body 104.

In addition, it is understandable that in the present disclosure the connection manner between the second casing body 104 and the base assembly 300 is not restricted to the threaded connection and can also be a rotating snap-fit connection or a pluggable connection, for example, the second casing body and the base assembly are connected in a rotating snap-fit manner, the second casing body can define a snap-in groove thereon, and, after the base assembly is screwed in the snap-in groove, the base assembly can continue rotating to drive the second casing body to rotate simultaneously, so as to close or open the liquid guide hole 1031 on the first casing body 103.

Figure 4:
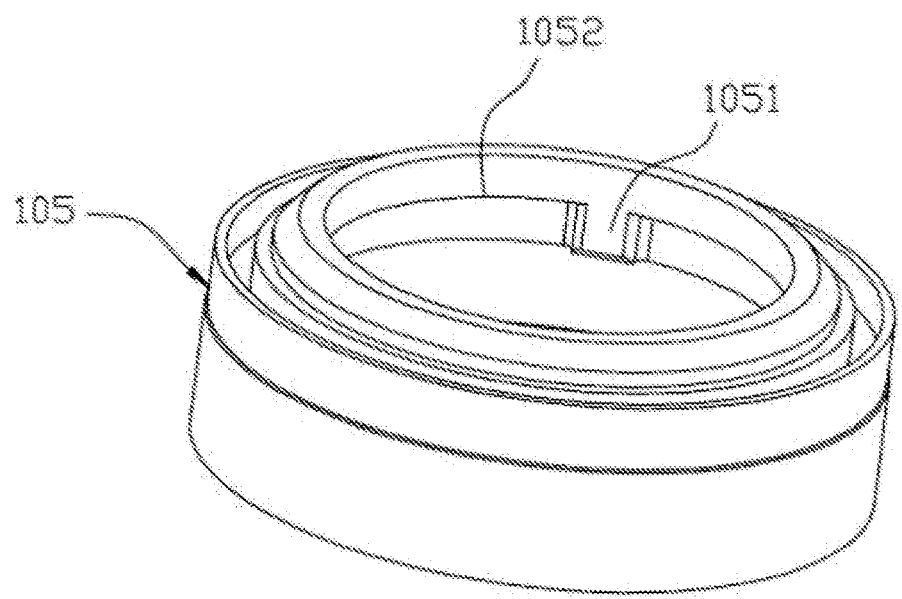
FIG. 4 is a structure diagram of a fixing sleeve according to an embodiment.

Referring to FIG. 3 and FIG. 4, the tobacco liquid chamber 101 has a fixing sleeve 105 disposed at the bottom thereof, the fixing sleeve 105 being configured for fixing the first casing body 103 and the second casing body 104. The fixing sleeve 105 is in tubular shape and is fixed on the housing unit 100. The second casing body 104 is capable of rotating relative to the fixing sleeve 105. The fixing sleeve 105 further has a step 1052 disposed on an inner side thereof. The second casing body 104 has a flange 1042 disposed on an outer sidewall thereof. When the second casing body 104 is inserted into the fixing sleeve 105 from the lower side of the fixing sleeve 105, the flange 1042 is blocked by the step 1052, which realizes the locating of the second casing body 104.

As a preferred scheme of the present embodiment, the flange 1042 has a rotation angle limit groove 1043 concaved inwards, and the step of the fixing sleeve 105 has a stop block 1051 disposed on an inner side thereof, the stop block 1051 being matched with the rotation angle limit groove 1043. The stop block 1051 is restricted within the arc angle of the rotation angle limit groove 1043 to move. Since the fixing sleeve 105 is fixed, the second casing body 104 is restricted within the rotation angle limit groove 1043 to move. In the present embodiment, the rotation angle limit groove 1043 has a corresponding arc angle of 45 degrees, that is to say, the second liquid guide hole 1041 on the second casing body 104 and the first liquid guide hole 1031 on the first casing body 103 are staggered by is a maximum angle of 45 degrees.

Figure 2:
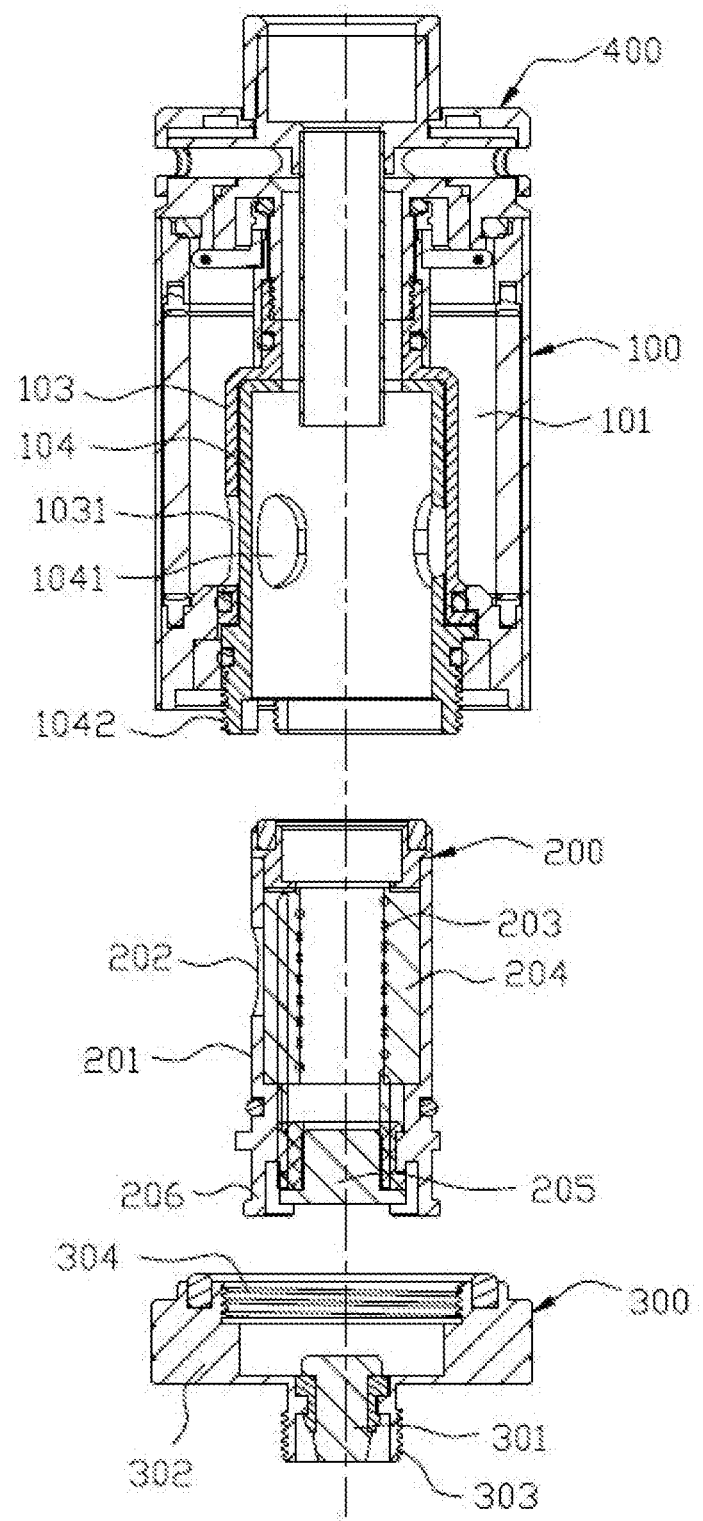
FIG. 2 is a diagram illustrating a state in which a base assembly and an atomization device are detached from a housing unit in an atomizer provided by an embodiment.
Figure 5:
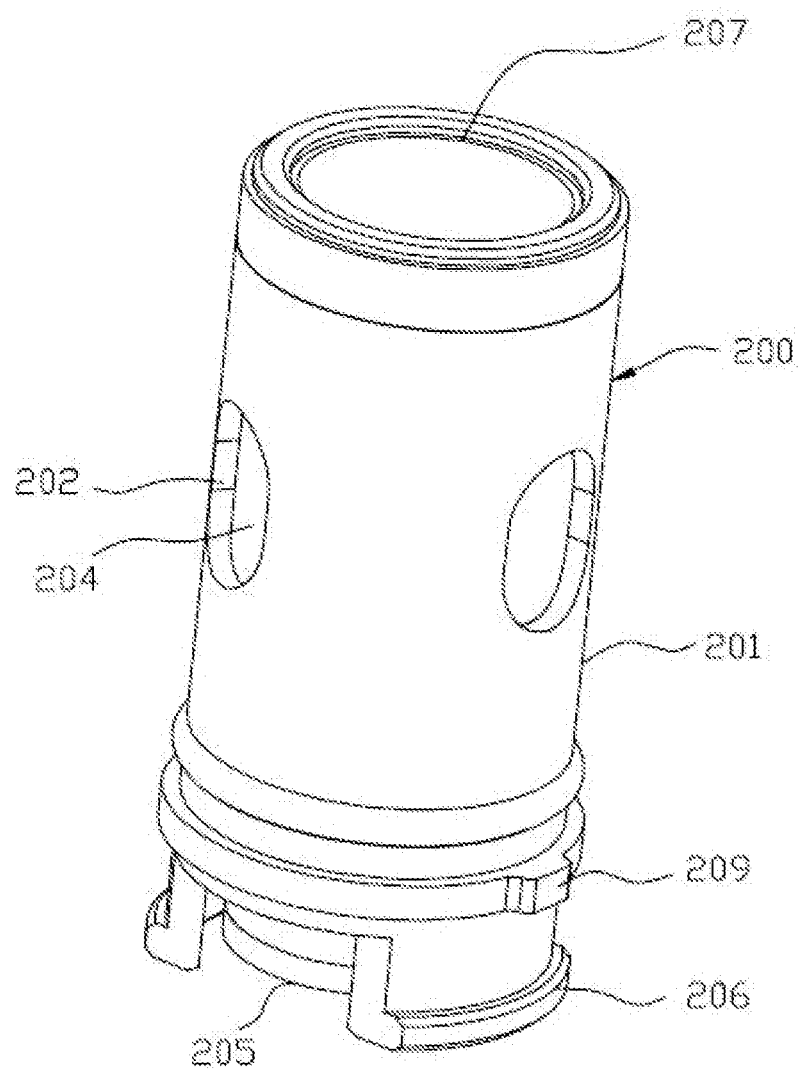
FIG. 5 is a structure diagram of an atomization device according to an embodiment.

Referring to FIG. 2, FIG. 3 and FIG. 5, the second casing body 104 defines a notch 1045 in a lower end thereof. The notch 1045 is located on the threaded portion 1044. The atomization device 200 has a projecting portion 209 disposed on an outer sidewall thereof, and, when the atomization device 200 is inserted in to the second casing body 104, the projecting portion 209 enters the notch 1045 so as to prevent rotation occurring between the atomization device 200 and the second casing body 104.

The atomization device 200 in the present embodiment includes an outer sleeve 201, a heating element 203 located in the outer sleeve 201, and a liquid storage layer 204 surrounding the periphery of the heating element 203. The heating element 203 employs a vertically arranged spiral heating wire preferably. The liquid storage layer 204 employs a porous material such as fiber cotton, non-woven fabric and microporous ceramic. The liquid storage layer 204 is capable of absorbing tobacco liquid and storing a small amount of tobacco liquid to supply to the spiral heating wire. The liquid storage layer 204 surrounds the periphery of the spiral heating wire, thereby defining a discharge channel for aerosol. The spiral heating wire is configured for heating the tobacco liquid on the liquid storage layer 204 to generate an aerosol, which is emitted into the discharge channel. The outer sleeve 201 defines an opening 207 in the top thereof. The aerosol can flow out from the opening 207 and the airflow opening 1046 at the top end of the second casing body 104 in sequence.

The outer sleeve 201 defines a plurality of liquid inlet holes 202 in a side wall thereof, and the liquid inlet hole 202 is capable of communicating with the first liquid guide hole 1031 and the second liquid guide hole 1041. Since relative rotation is forbidden between the atomization device 200 and the second casing body 104, the second liquid guide hole 1041 and the liquid inlet hole 202 are always aligned and in communication. When the second liquid guide hole 1041 is opened, the tobacco liquid in the tobacco liquid chamber 101 enters the liquid storage layer 204 from the first liquid guide hole 1031, the second liquid guide hole 1041 and the liquid inlet hole 202 in sequence.

Referring to FIG. 2, the base assembly 300 includes an outer threaded sleeve 302 configured to be in threaded connection with the second casing body 104, and an electrode column 301 located at the center of the outer threaded sleeve 302 and insulated from the outer threaded sleeve 302. The outer threaded sleeve 302 has internal threads 304 disposed at an upper part thereof, and the internal threads 304 are configured for connecting to the second casing body 104. The outer threaded sleeve 302 has external threads 303 disposed at a bottom part thereof, and the external threads 303 are configured for connecting to an external power supply module to be assembled into an electronic cigarette.

Correspondingly, the atomization device 200 includes an outer electrode portion 206 configured to be abutted against the outer threaded sleeve 302 and an inner electrode portion 205 configured to be abutted against the electrode column 301. The outer electrode portion 206 is actually one part of the outer sleeve 201. An insulating ring is disposed between the inner electrode portion 205 and the outer electrode portion 206. When the base assembly 300 is abutted against the bottom of the atomization device 200 and is rotated, the outer electrode portion 206 and the inner electrode portion 205 can generate a friction force relative to the base assembly 300.

FIG. 2 shows a state in which the base assembly 300 is detached. In conjunction with the description of the structure of the atomizer 10 described above, the principle of opening or closing the tobacco liquid chamber 101 when replacing the atomization device 200 is as follows.

In normal usage, the first liquid guide hole 1031 on the first casing body 103, the second liquid guide hole 1041 on the second casing body 104, and the liquid inlet hole 202 on the atomization device 200 are all in communication, and the tobacco liquid can enter the atomization device 200 directly.

When the atomization device 200 needs to be replaced, a user screws off the base assembly 300. Since the thread engagement between the second casing body 104 and the base assembly 300 has certain friction force, the base assembly 300 first drives the second casing body 104 and the atomization device 200 to rotate together, by means of the friction force between the outer threaded sleeve 302 and the outer electrode portion 206 and the friction force between the electrode column 301 and the inner electrode portion 205, so that the first liquid guide hole 1031 and the second liquid guide hole 1041 are staggered. Only when the second casing body 104 rotates to a limit position of the rotation angle limit groove 1043, the base assembly 300 can be screwed off the threads on the second casing body 104, and then the atomization device 200 can be taken out. In this condition, the tobacco liquid in the tobacco liquid chamber 101 cannot flow out, and user experience is improved.

After the atomization device 200 is replaced, the user can screw on the base assembly 300 again. The base assembly 300 is first screwed on the second casing body 104 through a thread, and then the base assembly 300 continues being rotated to drive the second casing body 104 and the atomization device 200 to rotate together, so that the first liquid guide hole 1031 and the second liquid guide hole 1041 are overlapped. In this condition, the tobacco liquid in the tobacco liquid chamber 101 can flow into the atomization device 200, and the atomization device 200 can work normally.

Figure 6:
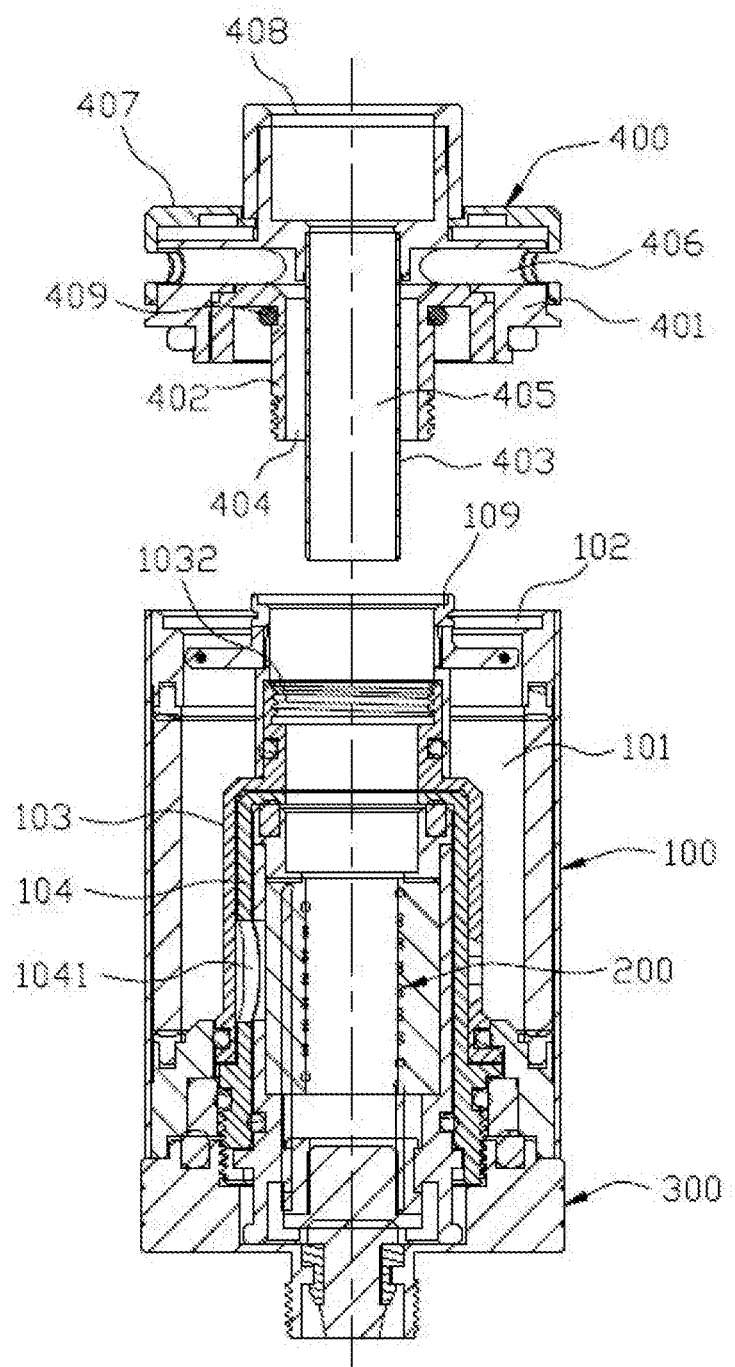
FIG. 6 is a diagram illustrating a state in which a cover body assembly is detached from a housing unit in an atomizer provided by an embodiment.

Referring to FIG. 6, the atomizer 10 provided by the present embodiment further has a liquid refill function. The atomizer 10 further includes a cover body assembly 400 detachably connected to an upper end of the housing unit 100. The tobacco liquid chamber 101 defines a liquid refill port 102 configured for refilling tobacco liquid in an upper part thereof, and the covey body assembly 400 is configured for sealing the liquid refill port 102. A user can detach the cover body assembly 400 and fill a tobacco liquid of his/her favorite flavor into the tobacco liquid chamber 101 through the liquid refill port 102 using a tobacco liquid container.

The cover body assembly 400 is configured to be in linkage with the first casing body 103. The first casing body 103 and the second casing body 104 are two independent mechanisms. Similar to the second casing body 104, the first casing body 103 also is capable of rotating relative to the housing unit 100 and is fixed by the fixing sleeve 105. While the cover body assembly 400 is detached from the housing unit 100, the cover body assembly 400 is capable of driving the first casing body 103 to rotate and allowing the first liquid guide hole 1031 to be staggered from the second liquid guide hole 1041, thereby allowing the first liquid guide hole 1031 to be closed and preventing the tobacco liquid flowing into the atomization device 200 to lead to leakage of tobacco liquid during the refill of tobacco liquid. While the cover body assembly 400 is assembled on the housing unit 100, the cover body assembly 400 also is capable of driving the first casing body 103 to rotate and allowing the first liquid guide hole 103 to be opened, so that the atomizer works normally.

Referring to FIG. 1 and FIG. 6, the cover body assembly 400 in the present embodiment includes a cover body 401, an outer tube 402 connected to the cover body 401, and an inner tube 403 located in the outer tube 402, the outer tube 402 being configured to be in threaded connection with the first casing body 103. A sealing ring 409 is disposed on the outer tube 402. A connecting sleeve 109 is connected to an upper end of the first casing body 103 and is capable of rotating with the first casing body 103. FIG. 1 shows a state illustrating that the first liquid guide hole 1031 on the first casing body 103 is opened. FIG. 6 shows a state illustrating that the first liquid guide hole 1031 on the first casing body 103 is closed.

When it is needed to refill tobacco liquid, a user screws off the cover body assembly 400. Since the thread engagement between the outer tube 402 and the first casing body 103 has a certain friction force, the cover body assembly 400 drives the first casing body 103 to rotate by means of the friction force between the sealing ring 409 and the connecting sleeve 109, so that the first liquid guide hole 1031 is closed. After the tobacco liquid chamber is filled with tobacco liquid, the user screws on the cover body assembly 400. After the cover body assembly 400 is screwed on the first casing body 103, the cover body assembly 400 continues being rotated to drive the first casing body 103 to the original position, so that the first liquid guide hole 1031 is opened again.

The inner tube 403 extends into the first casing body 103 and is aligned to the atomization device 200. The cover body 401 has an air inlet 406 disposed thereon. The cover body 401 is further mounted with an adjusting cover 407 configured for adjusting the volume of air entering the air inlet 406. An annular space is defined between the inner tube 403, the outer tube 402 and the first casing body 103, the annular space forms an air inlet passage 404. The air inlet passage 404 is configured to be in communication with the air inlet 406. An inner cavity of the inner tube 403 defines an air outlet passage 405. The cover body 401 further has a mouthpiece 408 disposed on an upper end thereof. The mouthpiece 408 is in communication with the air outlet passage 405. The inner tube 403 extends into the airflow opening 1046 of the second casing body 104 from the inside of the first casing body 103. When inhaling, air enters from the upper end of the atomizer 10 and flows downwards along the air inlet passage 404; then the air deflects to flow into the air outlet passage 405 above the atomization device 200 and carries the aerosol generated in the atomization device 200. Therefore, the air flow does not blow towards the heating element 203 directly, and the aerosol generated in the atomization device 200 is not reduced.

Figure 7:
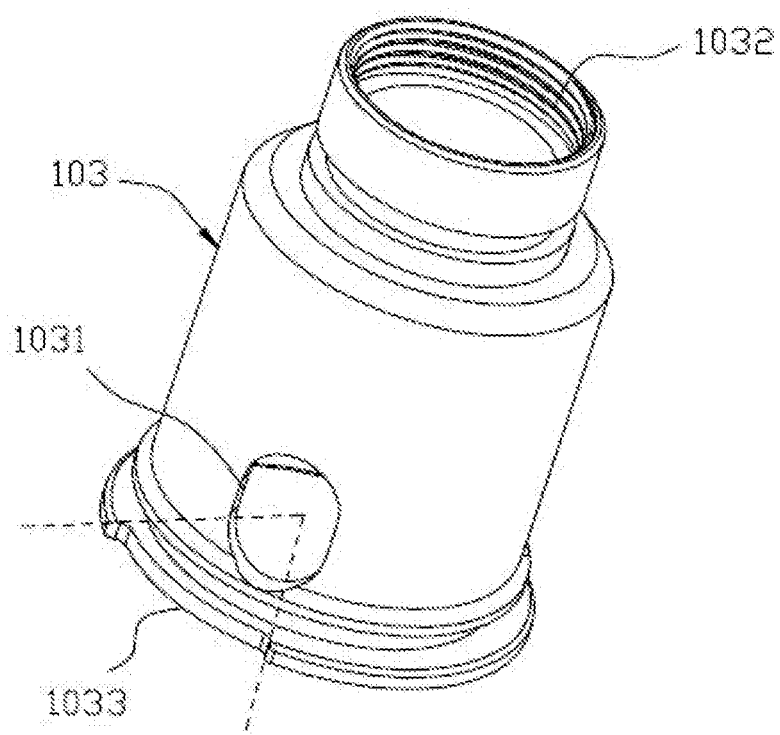
FIG. 7 is a structure diagram of a first casing body according to an embodiment.

Referring to FIG. 7, the first casing body 103 has a plurality of screw threads 1032 disposed on an inner wall at the upper end thereof. The screw threads 1032 are configured for connecting to the cover body assembly 400. The first casing body 103 defines an arc groove 1033 on a lower edge thereof, the arc groove 1033 being configured for limiting the range of rotation angle of the first casing body 103. When the atomizer is assembled, the first casing body 103 enters from the lower side of the fixing sleeve 105, allowing the stop block 1051 to move in the arc groove 1033, thereby restricting the angle of rotation of the first casing body 103. Similar to the second casing body 104, the arc groove 1033 has an angle of 45 degrees preferably in the present embodiment.

Figure 8:
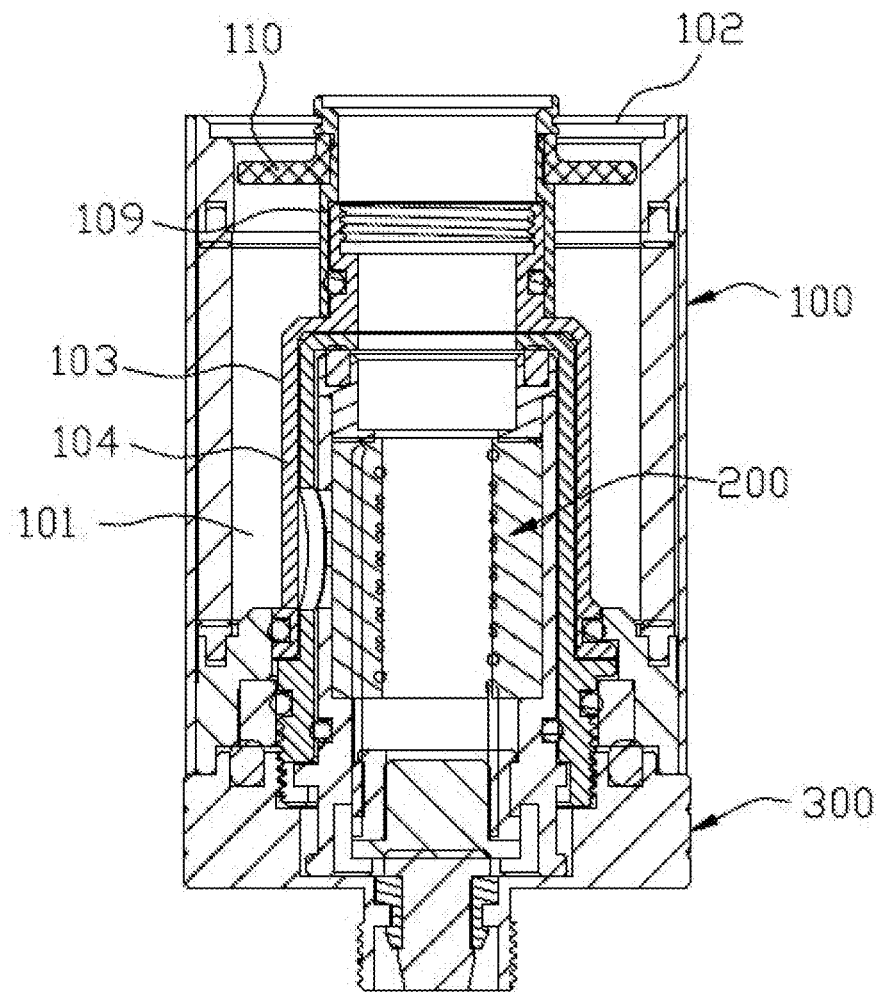
FIG. 8 is a diagram illustrating a state in which an elastic sealing ring is not detached from a connecting sleeve according to an embodiment.

Referring to FIG. 8, the atomizer 10 provided by the present embodiment further includes a function preventing leakage of tobacco liquid when the atomizer 10 is inclined. Specifically, the liquid refill port 102 is detachably mounted with a side leakage-proof assembly internally. The side leakage-proof assembly includes a deformable elastic sealing ring 110. The elastic sealing ring 110 is configured for sealing the liquid refill port 102. When a user refills tobacco liquid, the user first needs to screw off the cover body assembly 400 disposed on the upper end to expose the elastic sealing ring 110, and then the user puts a liquid refill nozzle of a liquid refill container into the liquid refill port 102 to push open the elastic sealing ring 110, so as to refill tobacco liquid into the tobacco liquid chamber 101. After the liquid refill nozzle of the liquid refill container is removed from the liquid refill port 102, the elastic sealing ring 110 recovers from deformation and seals the liquid refill port 102 automatically. The side leakage-proof assembly is capable of preventing tobacco liquid leaking and flowing from the liquid refill port 102 when the housing unit 100 is inclined or incorrectly operated.

The side leakage-proof assembly further includes a connecting sleeve 109 configured for fixing the elastic sealing ring 110. The connecting sleeve 109 is detachably connected to the first casing body 103. The elastic sealing ring 110 is sleeved on the connecting sleeve 109. In this embodiment, the connecting sleeve 109 is assembled on the upper end of the first casing body 103 in interference fit, and, when necessary, the connecting sleeve 109 and the elastic sealing ring 110 can be detached together.

As a preferred scheme, the connecting sleeve 109 defines an annular groove 111 configured for fixing the elastic sealing ring 110 in an outer sidewall thereof. The elastic sealing ring 110 is a silicone sheet. The silicone sheet extends outwards along a radial direction from the inside of the annular groove 111 and is filled into the liquid refill port 102. The annular groove 111 is capable of preventing the elastic sealing ring 110 sliding up and down.

Figure 9:
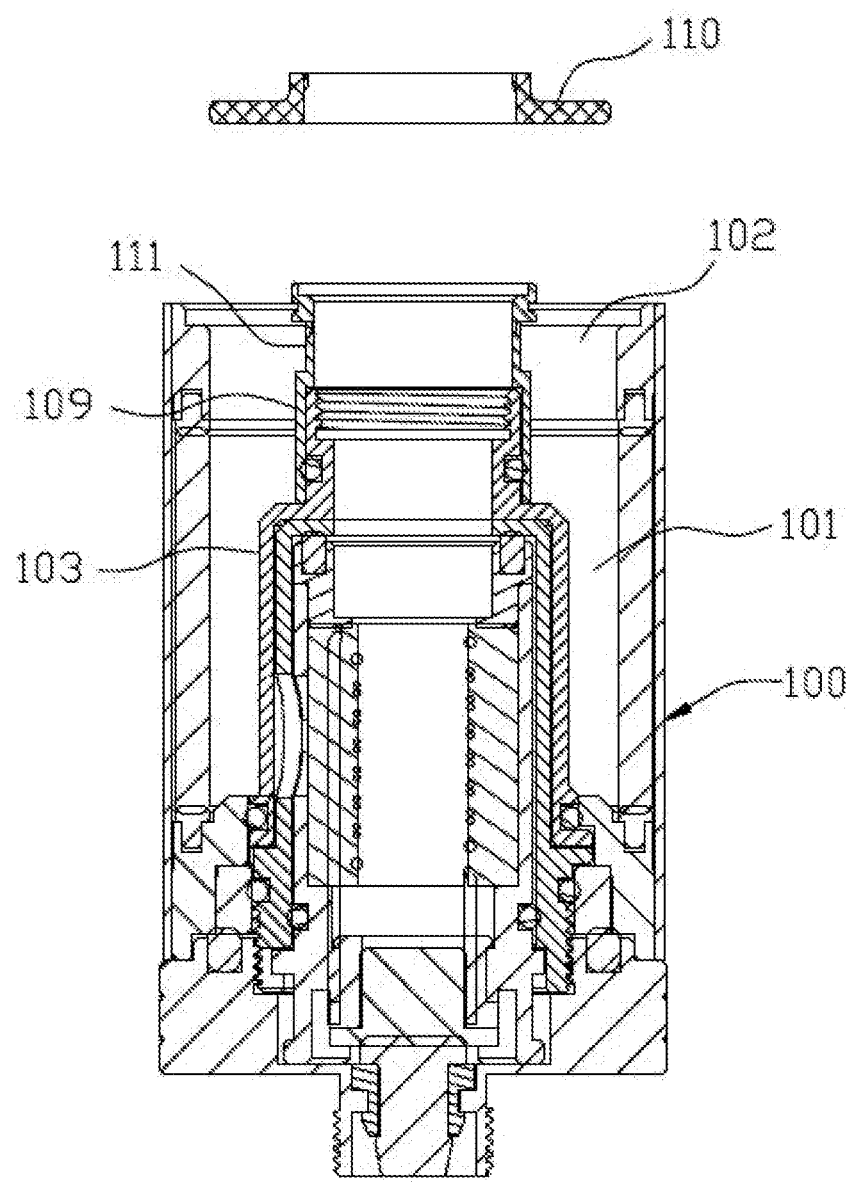
FIG. 9 is a diagram illustrating a state in which an elastic sealing ring is detached from a connecting sleeve according to an embodiment.

Referring to FIG. 9, a user can reserve or remove the elastic sealing ring 110 according to his/her usage habit. For example, if a user does not like the design of the side leakage-proof function on the atomizer, the user can remove the elastic sealing ring 110 from the annular groove 111 of the connecting sleeve 109. The operation is simple. After the elastic sealing ring 110 is removed, the user can refill tobacco liquid according to a regular atomizer. Other functions of the atomizer are not influenced.

Figure 10:
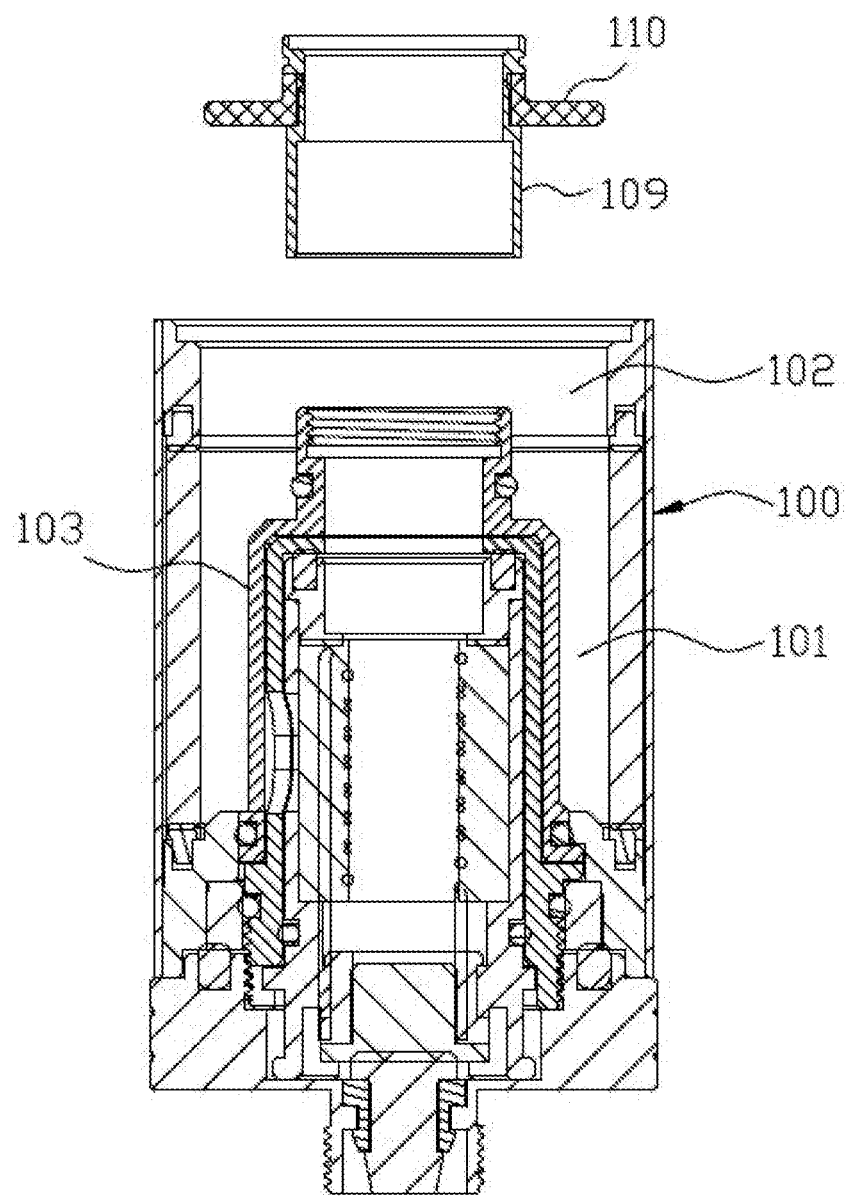
FIG. 10 is a diagram illustrating a state in which a connecting sleeve and an elastic sealing ring are detached from a first casing body according to an embodiment.

Referring to FIG. 10, when a user is to refill tobacco liquid or finds that the tobacco liquid chamber 101 is dirty, the user can pull out the whole side leakage-proof assembly, that is, remove the connecting sleeve 109 and the elastic sealing ring 110 together, so as to clean the tobacco liquid chamber 101.

The above embodiments are merely partial implementations listed in the description to help understand the content of the present disclosure, and they neither restrict the technical scheme of the present disclosure, nor make an exhaustion of all schemes implementable. Any minor improvements or equivalent substitutions made to the structures, processes or steps of the present disclosure are intended to be included in the scope of protection of the present disclosure.

What is claimed is:
1. An atomizer for an electronic cigarette, comprising:
 a housing unit, the housing unit defining therein a tobacco liquid chamber configured for storing tobacco liquid;
 a first casing body located in the tobacco liquid chamber, the first casing body defining thereon a first liquid guide hole configured for allowing the tobacco liquid to pass through;
 an atomization device located inside the first casing body, the atomization device being configured for aerosolizing the tobacco liquid to generate an aerosol for a user to inhale, the atomization device defining a liquid inlet hole allowing the tobacco liquid to pass through;
 a control valve, the control valve being configured for closing or opening the first liquid guide hole to control the tobacco liquid to enter the atomization device; the control valve defining a second liquid guide hole thereon; and
 a base assembly detachably connected to the housing unit and supporting the atomization device, the base assembly being configured to be in linkage with the control valve, the base assembly being capable of driving the control valve to close the first liquid guide hole while the base assembly is detached from the housing unit, and the base assembly being capable of driving the control valve to open the first liquid guide hole while the base assembly is assembled on the housing unit,
 wherein relative rotation between the atomization device and the control valve is forbidden so that the second liquid guide hole and the liquid inlet hole are always aligned and in communication;
 wherein the control valve comprises a second casing body located between the first casing body and the atomization device, the second casing body defines thereon the second liquid guide hole configured for allowing the tobacco liquid to pass through, and the base assembly is capable of driving the second casing body to rotate so that the second liquid guide hole and the first liquid guide hole are staggered or overlapped;

wherein the second casing body defines a notch at a lower end thereof, the atomization device has a projecting portion disposed on an outer side thereof, and, when the atomization device is inserted into the second casing body, the projecting portion enters the notch so as to prevent rotation occurring between the atomization device and the second casing body.

2. The atomizer according to claim 1, wherein the second casing body is configured to be in threaded connection with the base assembly, and the second casing body has a threaded portion disposed at the lower end thereof.

3. The atomizer according to claim 1, wherein the tobacco liquid chamber has a fixing sleeve disposed at the bottom thereof, the fixing sleeve being configured for fixing the first casing body and the second casing body, and wherein the second casing body is capable of rotating relative to the fixing sleeve.

4. The atomizer according to claim 3, wherein the second casing body has a flange disposed on a side wall thereof, the flange has a rotation angle limit groove concaved inwards, and the fixing sleeve has a stop block disposed on an inner side thereof, the stop block being matched with the rotation angle limit groove.

5. The atomizer according to claim 4, wherein the rotation angle limit groove has a corresponding arc angle of 45 degrees.

6. The atomizer according to claim 2, wherein the base assembly comprises an outer threaded sleeve configured to be in threaded connection with the second casing body, and an electrode column located at the center of the outer threaded sleeve and insulated from the outer threaded sleeve.

7. The atomizer according to claim 6, wherein the atomization device comprises an outer electrode portion configured to be abutted against the outer threaded sleeve and an inner electrode portion configured to be abutted against the electrode column.

8. The atomizer according to claim 1, wherein the atomization device comprises an outer sleeve, a heating element located in the outer sleeve, and a liquid storage layer surrounding a periphery of the heating element.

9. The atomizer according to claim 8, wherein the outer sleeve defines the liquid inlet hole in a side wall thereof, the liquid inlet hole being capable of communicating with the first liquid guide hole and the second liquid guide hole.

10. The atomizer according to claim 1, further comprising a cover body assembly detachably connected to an upper end of the housing unit, the tobacco liquid chamber defining a liquid refill port configured for refilling tobacco liquid in an upper part thereof, and a cover body assembly being configured for sealing the liquid refill port.

11. The atomizer according to claim 10, wherein the cover body assembly is configured to be in linkage with the first casing body; while the cover body assembly is detached from the housing unit, the cover body assembly is capable of driving the first casing body to rotate and allowing the first liquid guide hole to be closed, thereby preventing the tobacco liquid flowing into the atomization device; and, while the cover body assembly is assembled on the housing unit, the cover body assembly is capable of driving the first casing body to rotate and allowing the first liquid guide hole to be opened.

12. The atomizer according to claim 11, wherein the cover body assembly comprises a cover body, an outer tube connected to the cover body, and an inner tube located in the outer tube, the outer tube being configured to be in threaded connection with the first casing body.

13. The atomizer according to claim 12, wherein the first casing body has a plurality of screw threads disposed on an inner wall at an upper end thereof and defines an arc groove on a lower edge thereof, the arc groove being configured for limiting a range of rotation angle of the first casing body.

14. The atomizer according to claim 13, wherein the arc groove has an angle of 45 degrees.

15. The atomizer according to claim 12, wherein the inner tube extends into the first casing body and is aligned to the atomization device, the cover body has an air inlet disposed thereon; an annular space is defined between the inner tube, the outer tube, and the first casing body, the annular space forms an air inlet passage, the air inlet passage is configured to be in communication with the air inlet, and the inner tube defines an air outlet passage therein.

16. An atomizer for electronic cigarette comprising:
a housing unit, the housing unit defining therein a tobacco liquid chamber configured for storing tobacco liquid, and the tobacco liquid chamber having a liquid refill port;
a first casing body located in the tobacco liquid chamber, the first casing body defining thereon a first liquid guide hole configured for allowing the tobacco liquid to pass through;
an atomization device located inside the first casing body, the atomization device being configured for aerosolizing the tobacco liquid to generate an aerosol for a user to inhale; and
a cover body assembly detachably connected to the housing unit and sealing the liquid refill port, the cover body assembly being configured to be in linkage with the first casing body; while the cover body assembly is detached from the housing unit, the cover body assembly being capable of driving the first casing body to rotate and allowing the first liquid guide hole to be closed, thereby preventing the tobacco liquid from flowing into the atomization device; and, while the cover body assembly is assembled on the housing unit, the cover body assembly being capable of driving the first casing body to rotate and allowing the first liquid guide hole to be opened;
wherein the cover body assembly comprises a cover body, an outer tube connected to the cover body, and an inner tube located in the outer tube, the outer tube being configured to be in threaded connection with the first casing body.

* * * * *